United States Patent [19]

Lux et al.

[11] 4,162,875
[45] Jul. 31, 1979

[54] DECALCIFICATION CABINET FOR OSSEOUS AND DENTAL SPECIMENS

[75] Inventors: Virginia J. Lux, Dover, Del.; Peter J. Tsaknis, Mt. Airy, Md.

[73] Assignee: The United States of America as represented by the Secretary of the Army, Washington, D.C.

[21] Appl. No.: 900,388

[22] Filed: Apr. 26, 1978

[51] Int. Cl.$^2$ .............................................. B01F 13/08
[52] U.S. Cl. .................................. 366/273; 134/143; 422/266; 220/20.5
[58] Field of Search ............... 366/273, 274; 128/2 R, 128/272; 195/127; 422/239, 297, 266, 102, 277; 134/143, 165, 201; 220/20.5; 4/DIG. 4

[56] References Cited

U.S. PATENT DOCUMENTS

| 2,350,534 | 6/1944 | Rosinger | 366/274 |
| 3,250,283 | 5/1966 | Reinfeld | 134/201 |
| 3,614,959 | 10/1971 | Schollmaier | 366/274 |

FOREIGN PATENT DOCUMENTS 645941  9/1962  Italy .......................................... 134/143

*Primary Examiner*—Robert W. Jenkins
*Attorney, Agent, or Firm*—William G. Gapcynski; Werten F. W. Bellamy; Sherman D. Winters

[57] ABSTRACT

A decalcification cabinet is provided for decalcifying osseous and dental material. The cabinet includes drawers in which the specimens are held and includes numerous holes in these drawers and in the sides and base to permit substantially free flow of a decalcifying liquid. The edges of the top of the cabinet extend laterally outwards from the cabinet sides so as to enable the cabinet to be suspended in a container of decalcifying solution. The cabinet top provides a closure to prevent the escape of fumes and the cabinet is suspended such that a stirring magnet, for stirring the solution, can be positioned directly under the base of the cabinet.

4 Claims, 4 Drawing Figures

U.S. Patent
Jul. 31, 1979
4,162,875
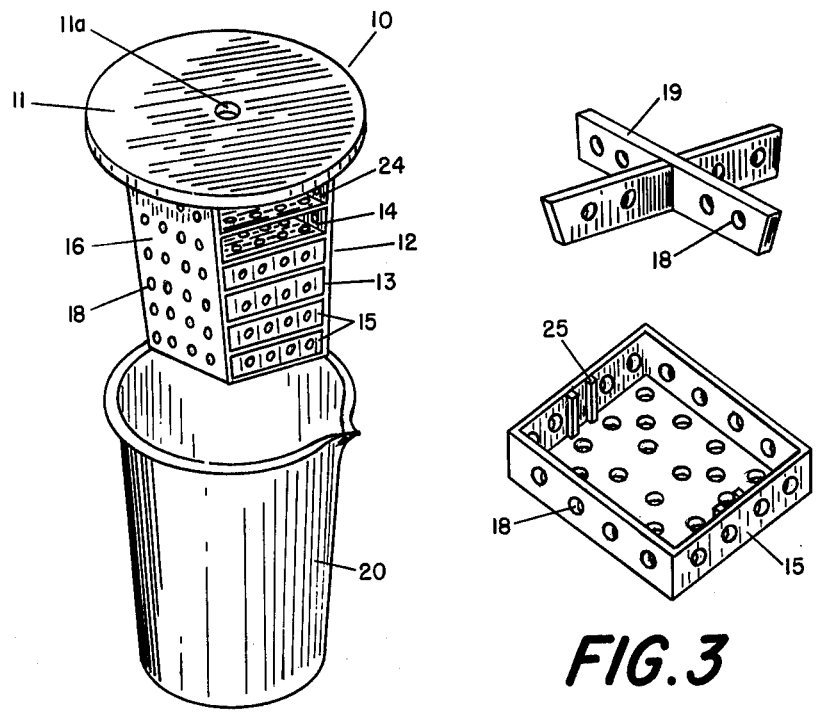
FIG. 1
FIG. 3
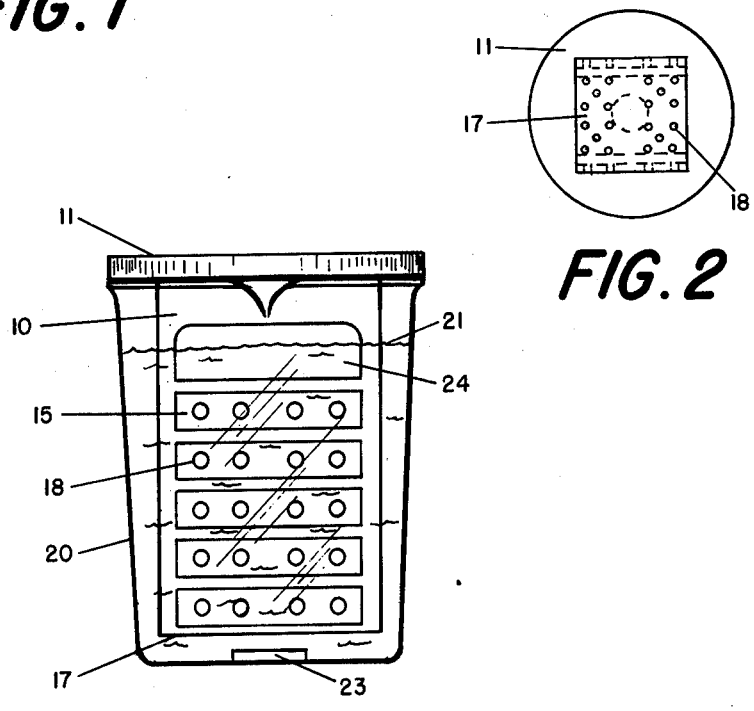
FIG. 2
FIG. 4

DECALCIFICATION CABINET FOR OSSEOUS AND DENTAL SPECIMENS

FIELD OF THE INVENTION

The invention relates to decalcifying methods and devices for the decalcification of osseous and dental specimens and, more specifically, to a decalcifying cabinet adapted to be suspended in a decalcifying solution and to hold multiple specimens.

BACKGROUND OF THE INVENTION

The decalcification of hard biological specimens such as bones and teeth has traditionally been a tedious, time consuming process. In accordance with conventional procedures, specimens are first wrapped in gauze and tied with a cord and, after appropriate identification tags are provided, are thereafter suspended in a beaker containing a decalcifying solution for the appropriate length of time. Such procedures require several minutes to wrap and tie each specimen and to label and secure the identification tag to the specimen, prior to decalcification. Following the actual decalcification, additional time is required in removing the specimen from the decalcifying solution, cutting the gauze wrapping to remove the enclosed specimen, and discarding the gauze and cord.

The large amount of unproductive time which is needed to wrap, tie, cut and unwrap each specimen becomes a particularly acute problem when a large number of samples or specimens are processed. In an average research project involving one hundred laboratory mice or rats, the time expended in accomplishing the decalcification of a single bone, such as the tibia, can be as much as fourteen to seventeen hours. Thus, it will be appreciated that in terms of the labor costs involved, the time required by a histopathology technician to process the specimens can be a significant expense.

Another disadvantage in the process described above concerns offensive and irritating liquid and fumes which result from spillage or other release of the decalcifying solution that is characteristic of the unwrapping step in processing the specimens.

As explained hereinbelow, the present invention generally concerns the provision of a perforated cabinet in which the specimens are held during decalcification. A sterilizing sink including a foraminous or perforated tray is disclosed in U.S. Pat. No. 653,714 (Thursman). Other patents of possible interest include U.S. Pat. No. D232,813 (Myers) and U.S. Pat. No. D238,931 (DuMolin).

SUMMARY OF THE INVENTION

In accordance with the invention, a decalcifying cabinet is provided for decalcifying osseous and dental materials. The cabinet comprises a top portion and a base portion, the latter including a plurality of drawers therein in which specimens are stored. The base portion and drawers of the cabinet contain a plurality of holes to permit substantially unimpeded flow of a decalcifying solution therethrough so as to provide an even distribution of the solution. The top portion of the cabinet extends laterally outwardly beyond the base portion to enable the cabinet to be suspended in a container of the decalcifying solution.

The drawers of the cabinet are preferably provided with perforated partitions which divide the drawer in a plurality of sections for storing multiple specimens during processing.

The cabinet is positioned in a container of decalcifying solution with the top portion of the cabinet resting on the upper edges of the side walls of the container so as to suspend the cabinet within the solution and to provide a closure means for preventing the escape of fluids (i.e., fumes and liquid) from the container. Advantageously, the bottom of the cabinet is spaced from the bottom of the container so as to permit a stirring magnet to be positioned beneath the bottom of the cabinet, the magnet serving to provide circulation of the decalcifying solution.

The cabinet is preferably of unitary construction and is fabricated from a high density polyethylene plastic material so as to resist corrosive destruction of the cabinet by the acidic decalcifying solutions. Alternatively, the cabinet can be constructed of individual sections cemented together with an appropriate solution-resistant adhesive.

In a specific embodiment, a cylindrical container, such as a beaker, is used and the top portion of the cabinet comprises a disc-shaped member which closes off the top of the beaker. This top portion preferably includes a hole in the center so that a hose can be inserted for rinsing the osseous and dental materials after the decalcification process has been completed.

Additional features and advantages of the invention will be set forth in, or apparent from, the detailed description of the preferred embodiments of the invention found hereinbelow.

BRIEF DESCRIPTION OF THE DRAWINGS

FIG. 1 is an exploded perspective view of a preferred embodiment of the decalcification cabinet of the present invention and a beaker used therewith;

FIG. 2 is a bottom plan view of the cabinet of FIG. 1;

FIG. 3 is an exploded perspective view of a drawer construction for the cabinet of FIG. 1 and;

FIG. 4 is a side elevational view of a perferred embodiment of the decalcification apparatus of the invention while in use.

DETAILED DESCRIPTION OF THE PREFERRED EMBODIMENTS

Referring to FIGS. 1 and 2, a preferred embodiment of the decalcifying cabinet of the present invention is shown. The cabinet, which is generally denoted 10, includes a generally circular top portion 11 with a rinsing hole 11a in the center. The cabinet 10 also comprises a box-like rectangular base portion 12 having a front side 13. Front side 13 includes a plurality of openings 14 in which a series of specimen drawers 15 are individually received. The side walls 16 of the cabinet and the base 17 (see FIG. 2) contain numerous holes 18 therein through which the decalcification solution can flow. A further enlarged opening 24 may also be provided at the top of the base portion 12 as described below.

Referring to FIG. 3, a preferred embodiment of a drawer construction for use in cabinet 10 is illustrated. Drawer 15, which corresponds to one of the drawers in FIG. 1, contains a plurality of holes 18 throughout. Cross-shaped partitions 19 are provided which are positioned in drawer 15 using guides 25 so as to divide the drawer into four parts. it will be evident that the holes 18 in the sides of drawers 15 coincide with, i.e., are aligned with, the holes in side walls 16 of base portion 12. Similarly, the holes 18 in base 17 coincide with the holes 18 in the bottom of the lowest drawer 15.

Referring to FIG. 4, cabinet 10 is shown positioned in a beaker 20 containing a decalcifying solution 21. As illustrated, the top 11 of the cabinet 10 rests upon the top edge of the beaker 20 thereby suspending the cabinet 10 in the decalcifying solution 21. The relative heights of cabinet 10 and beaker 20 are such that the base of cabinet 10 is spaced from, i.e., elevated above, the bottom of beaker 20. A stirring magnet 23 is positioned in this space below cabinet 10 to stir the solution 21 during the decalcification period. As noted, the cabinet 10 can also be provided with an opening 24 above the uppermost drawer 15 to aid in the circulation of the decalcifying solution and rinsing liquid.

The Cabinet 10 should be made from a material which is compatible with the decalcifying solution used with the specimens. It has been found that polyethylene plastic will resist continuous exposure to the inorganic and organic acids used in the decalcifying solution for up to thirty days or longer without any damage to the material. Other plastics, such as polycarbonate and plexiglass can also be employed, since constant exposure of these plastics to the decalcifying reagents causes little or no damage. In addition, the latter are less expensive and easier to cut than the polyethylene. All of the materials are commercially available and provide for easy construction of the cabinet.

The cabinet of the invention can be of unitary construction. Alternatively, the cabinet can comprise individual sections cemented together with an appropriate adhesive, i.e., an adhesive which is unaffected by the properties of the decalcifying solution.

One possible procedure for using the decalcification cabinet of the invention is as follows; First, the osseous and/or dental specimens to be decalcified are placed in specific compartments of the drawers 15 of the cabinet 10. The partitions 19 for drawers 15 may or may not be employed depending on the size of the specimens. Identification of the specimens can be made by placing a marker in the section containing the specimen or by noting down the position of the specimens in the cabinet in a laboratory notebook.

Once the specimens are in place, the cabinet 10 is placed in a container such as a beaker 20 holding the decalcifying solution 21 and having a stirring magent 23 in the base. The top 11 of the cabinet 10 rests on the top edges of the walls to the containers 20 so as to provide a cover or closure element for preventing liquid and fumes from escaping from the container during the decalcification step. The stirring magnet 23 is then activated in a conventional manner to cause circulation of the decalcifying solution and a consequent substantially even distribution of the solution throughout the cabinet 10, the liquid flowing in a largely unimpeded manner through the numerous holes 18 in the cabinet structure.

Following decalcification, a section of rubber tubing, connected at one end to a sink faucet nozzle, is inserted into the rinsing hole 11a in the top 11 of cabinet 10. This permits water to pass from the faucet directly into the cabinet thereby providing thorough rinsing of the specimens prior to their removal for further processing.

Use of the cabinet of the invention for the decalcification of osseous and dental materials enables the process to be carried out in a much more rapid and efficient manner than the time consuming procedure outlined above wherein individually wrapped specimens are used. Other advantages include the savings and convenience afforded by eliminating the use of gauze wrapping, cord and paper tags, especially when the cost and time spent are considered over an extended period of time. Also, no special akills or training is required to utilize the decalcification cabinet of this invention.

The decalcification cabinet can be successfully employed in all laboratory procedures wherein human or animal calcified tissues are processed for microscopic evaluation or other related applications. Moreover, it will be appreciated by those skilled in the art that although the invention has been described relative to exemplary embodiments thereof, variations and modifications can be made in these embodiments without departing from the scope and spirit of the invention.

We claim:

1. An apparatus for decalcifying osseous and dental tissues comprising a container of decalcifying solution, a cabinet including a top portion and base portion, said base portion including a plurality of drawers therein, said cabinet and drawers containing a plurality of holes therein through which a decalcifying solution can flow, said top portion having support edges which extend laterally outwardly from the sides of the base portion of the cabinet for suspending said cabinet in said container, said top portion of said container resting on the upper edges of the container so that said base portion is suspended within said solution above the base of the container and providing closure means for preventing the escape of fluids from said container, a stirring magnet for stirring the decalcifying solution being positioned in said solution beneath said cabinet.

2. The apparatus of claim 1 wherein the container comprises a cylinder having an opening at the upper end, and the top of the cabinet comprises a disc-shaped member which closes off said opening of said container.

3. The apparatus of claim 2 wherein said top includes a centrally located aperture for rinsing liquids.

4. The apparatus of claim 1 wherein said drawers include removable partition means for dividing said drawers into sections.

* * * * *